(12) United States Patent
Forsyth

(10) Patent No.: US 6,825,046 B1
(45) Date of Patent: Nov. 30, 2004

(54) MICRO EXTRACTION TECHNIQUE

(75) Inventor: Donald S. Forsyth, Metcalfe (CA)

(73) Assignee: Her Majesty the Queen in right of Canada, as represented by the Minister of Health, Ottawa (CA)

( * ) Notice: Subject to any disclaimer, the term of this patent is extended or adjusted under 35 U.S.C. 154(b) by 0 days.

(21) Appl. No.: 09/635,782

(22) Filed: Aug. 11, 2000

(30) Foreign Application Priority Data

Aug. 12, 1999 (CA) .............................................. 2280418

(51) Int. Cl.$^7$ ................................................ G01N 1/40
(52) U.S. Cl. ...................... 436/178; 436/161; 436/177; 422/69; 422/70; 422/101
(58) Field of Search ................................. 436/173, 161, 436/177; 422/58, 69, 70, 101

(56) References Cited

U.S. PATENT DOCUMENTS

| | | | | |
|---|---|---|---|---|
| 5,000,854 A | * | 3/1991 | Yang | ........................... 210/638 |
| 5,496,741 A | * | 3/1996 | Pawliszyn | ................... 436/163 |
| 5,565,622 A | * | 10/1996 | Murphy | |
| 5,576,217 A | * | 11/1996 | Hsu | ............................ 436/126 |
| 5,691,206 A | * | 11/1997 | Pawliszyn | |
| 5,693,228 A | * | 12/1997 | Koehler et al. | ............. 210/656 |
| 5,707,589 A | * | 1/1998 | Fullemann | ................... 422/99 |

FOREIGN PATENT DOCUMENTS

| | | |
|---|---|---|
| CA | 2300411 | 7/2000 |
| EP | 1 039 288 A2 | 9/2000 |

OTHER PUBLICATIONS

Fisher Scientific Catalog, 1988, pp. 142–143 and 1159–1163.*

* cited by examiner

Primary Examiner—Jan M. Ludlow
(74) Attorney, Agent, or Firm—J. Wayne Anderson

(57) ABSTRACT

The invention disclosed relates to a method and apparatus for solid phase microextraction of target analytes from solid or fluid samples. The apparatus comprises gas tight enclosure means, means for introducing a sample including target analytes into the enclosure means, and means located within the enclosure means for extracting the target analytes from the sample, wherein the extraction means either samples a head space near the sample or samples the sample directly.

22 Claims, 7 Drawing Sheets

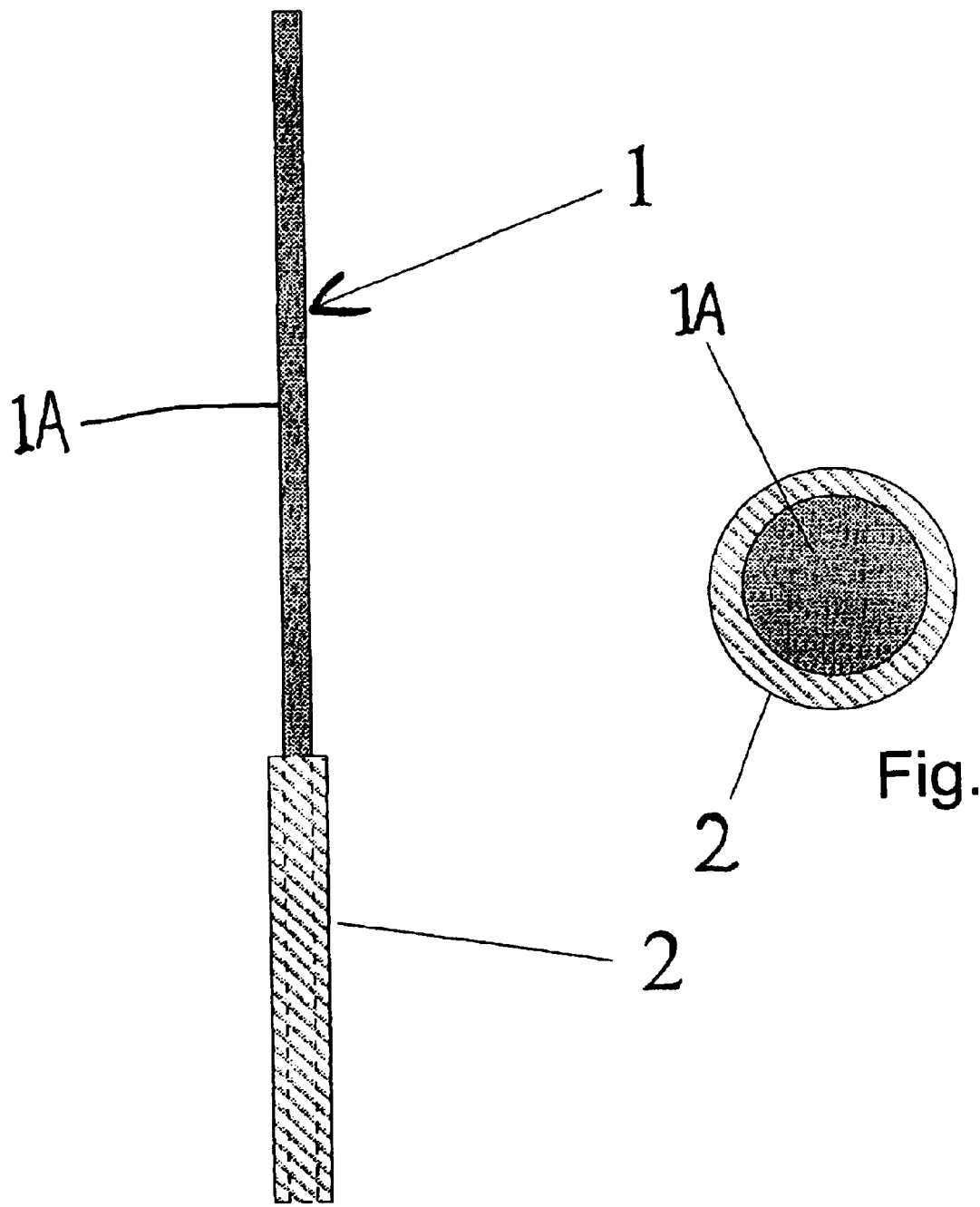

MICRO EXTRACTION TECHNIQUE

BACKGROUND OF THE INVENTION

1. Field of the Invention

This invention relates to the method for solid phase micro extraction and analysis and in particular to the micro extraction and analysis using various types of solid supports which can be coated with various materials.

2. Description of the Prior Art

The analysis of environmental, food, biomedical and pharmaceutical samples involves the separation of components or analytes of interest from the sample matrix such as soil, water, food, tissue or other material. Liquid/liquid extraction is a traditional method of sample extraction and separation—an example is the extraction of a water sample with an immiscible organic solvent such as hexane. Solid samples can be mixed with anhydrous sodium sulfate, ground to a free flowing powder, packed into a chromatography column and then extracted with an organic solvent. Solvent-based extraction methods are frequently time consuming and expensive since high purity solvents must be purchased and properly disposed. Also, many solvents are relatively toxic and should be handled only under proper laboratory conditions. Solvent extraction is not very selective so further analyte isolation is usually accomplished by other chromatographic techniques before the analytes can be quantitated. This increases the cost and complexity of the analysis.

Solid phase extraction is an alternative to liquid/liquid extraction. This involves the selective adsorption of the analytes of interest onto a solid substrate/sorbent (typically a chemically modified silica surface) while other co-extractives are unretained. Pre-made solid phase extraction cartridges are available but there is significant variation between manufacturers products. The analytes of interest are then eluted from the sorbent by the use of selective solvent or solvent mixtures. The analyte(s) can then be analyzed. Many different types of sorbents are available so that a wide range of selectivities are possible. Although solvent use is reduced relative to liquid/liquid extraction, purchase and disposal costs remain and the procedure is still time consuming.

U.S. Pat. No. 5,691,206 describes a prior solid phase micro extraction apparatus and method. The method consists of two process steps—partitioning of analytes between the coating (sorbent) and sample, and desorption of the collected analytes into an analytical instrument. This is accomplished by exposing the coated substrate, typically in the form of a fibre, to the sample, allowing the target analytes to be extracted e.g. adsorbed into the coating from either the head space above the sample or from the sample directly. Various coatings are available to adjust selectivity of the extraction and no solvent is used for the extraction. After exposure, the fibre (now containing concentrated analytes) is then typically moved to a thermal desorption instrument, where the analyte is thermally desorbed, followed by separation and quantitation of the analytes. The method is simple, inexpensive and eliminates some of the disadvantages of solid phase extraction including: solvent consumption, extract preconcentration and high blank values. However, it has a significant limitation of low sample throughput which has been only partially overcome by expensive automation options.

SUMMARY OF THE INVENTION

According to the invention, an apparatus and method for carrying out solid phase micro extraction of analytes contained within a fluid or a solid sample, is provided.

In one embodiment of the invention, an apparatus for carrying out solid phase microextraction of analytes included in a fluid or a solid sample is provided, comprising gas tight enclosure means, means for introducing a sample including target analytes into the enclosure means, and means located within the enclosure means for extracting the target analytes from the sample, wherein the extraction means either samples a head space near the sample or samples the sample directly.

In another embodiment of the invention, an apparatus is provided comprising, an assembly for carrying out solid phase microextraction of analytes contained within a fluid or a solid sample, and a gas tight sampling enclosure. The assembly is arranged such that it either samples the head space above the sample or samples the sample matrix directly, within the gas tight enclosure. The assembly includes a solid support, which may be in the form of a fibre which may be coated or uncoated. The fibre and/or the coating material is selected, based upon selectivity of the fibre and/or coating for at least one of the analytes present in the sample.

In a further embodiment of the invention, a method for solid phase micro extraction of analytes included in a fluid or a solid sample is provided, comprising (a) exposing a fluid or a solid sample including target analytes, to a solid support which may be coated or uncoated, the support and/or the coating being selected based upon selectivity of the support and/or coating for at least one of the analytes in the sample, for a sufficient time to permit chemical extraction of the analytes by the support to occur, and (b) ending said contact and then placing said solid support into a micro volume of solvent where chemical desorption of the analytes from the support occurs.

In yet another embodiment of the invention, a method is provided for solid phase micro extraction of analytes contained within a fluid or a solid sample, comprising exposing a solid support, which may be in the form of a fibre, which may be coated or uncoated, the fibre and/or the coating material being selected based upon selectivity of the fibre and/or coating for at least one of the analytes in the sample, for a sufficient time to permit chemical extraction of the analytes to occur, ending said contact and then placing said solid support into a suitable micro volume of solvent where desorption of the analytes from the support occurs. Quantitation of the analytes in the extracting solvent can then proceed by conventional means.

BRIEF DESCRIPTION OF THE DRAWINGS

FIG. 1 is a schematic side view of a fibre assembly according to the invention;

FIG. 2 is an enlarged end view of a fibre assembly according to the invention;

DETAILED DESCRIPTION OF THE INVENTION

Referring to FIGS. 1 and 2, in detail, an assembly 1 for carrying out solid phase micro extraction is shown, comprising a cylindrical support 1A, which may be in the form of a fibre, and which may have a length of coating 2 of which various types of organic compounds could be used. The diameter of the fibre may vary, but would generally be between 0.5 to 2 mm and it may be solid or hollow.

Figure 3:
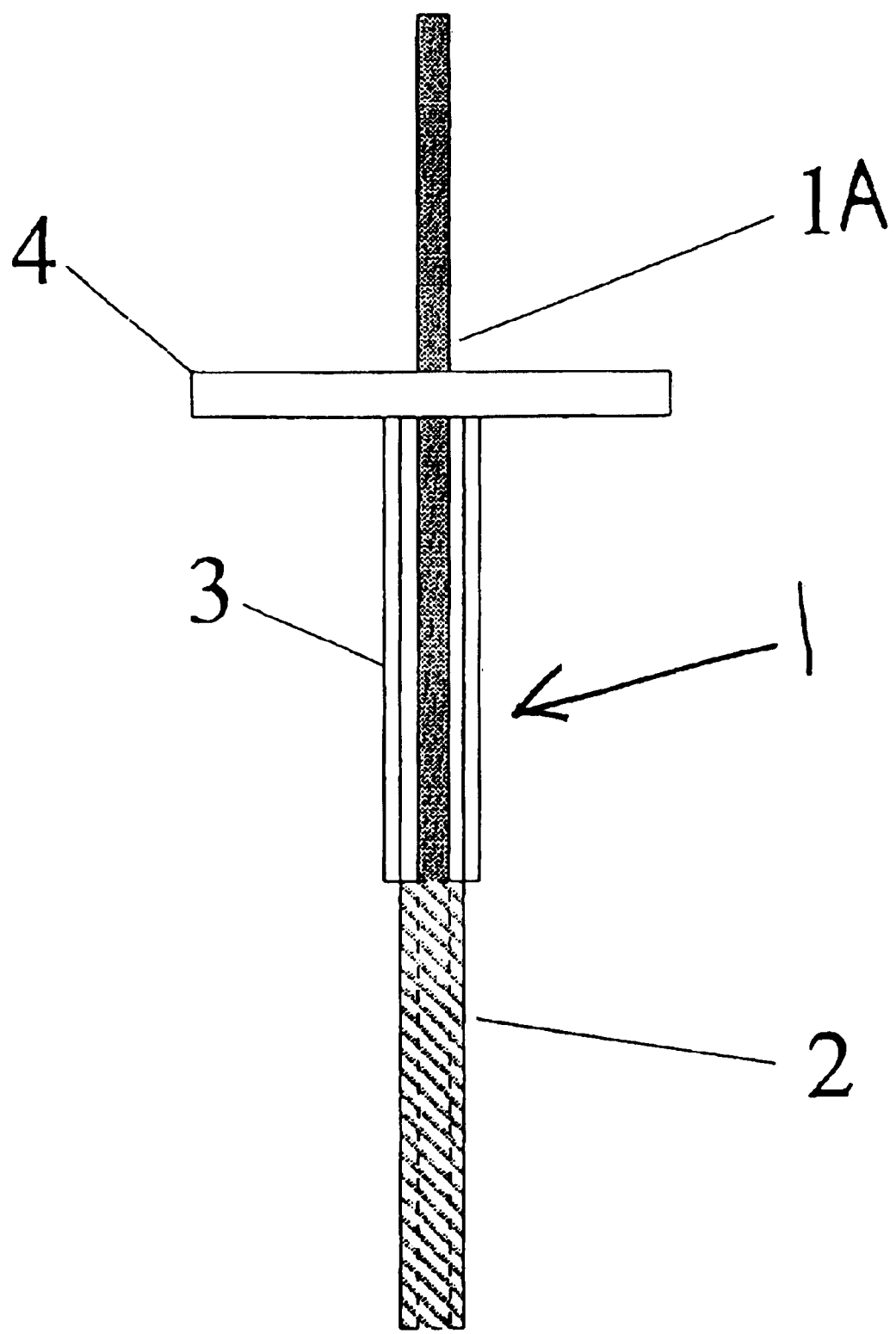
FIG. 3 is a schematic side view of a shielded fibre assembly according to the invention.

As seen in FIG. 3, a cylindrical support 1A which has a length of coating, is mounted through a Teflon® faced silicone septum 4. Stainless steel tubing 3, which acts as a shield, of slightly longer length than the coating is mounted over the support 1A. If the fibre is pulled up through the silicone septum, until the fibre coating is inside the stainless steel sleeve 3, the extracted analytes are shielded from volatizing into the atmosphere.

As shown in FIG. 3, the outer diameter of the fiber 2 and inner diameter of the tube 3 align for a tight fit.

This permits short term storage or transport of the fibre assembly without having to immediately desorb the analytes into a solvent.

The coating is typically provided on the outside of solid fibres, and may be on the outside and/or the inside of hollow fibres.

Figure 4:
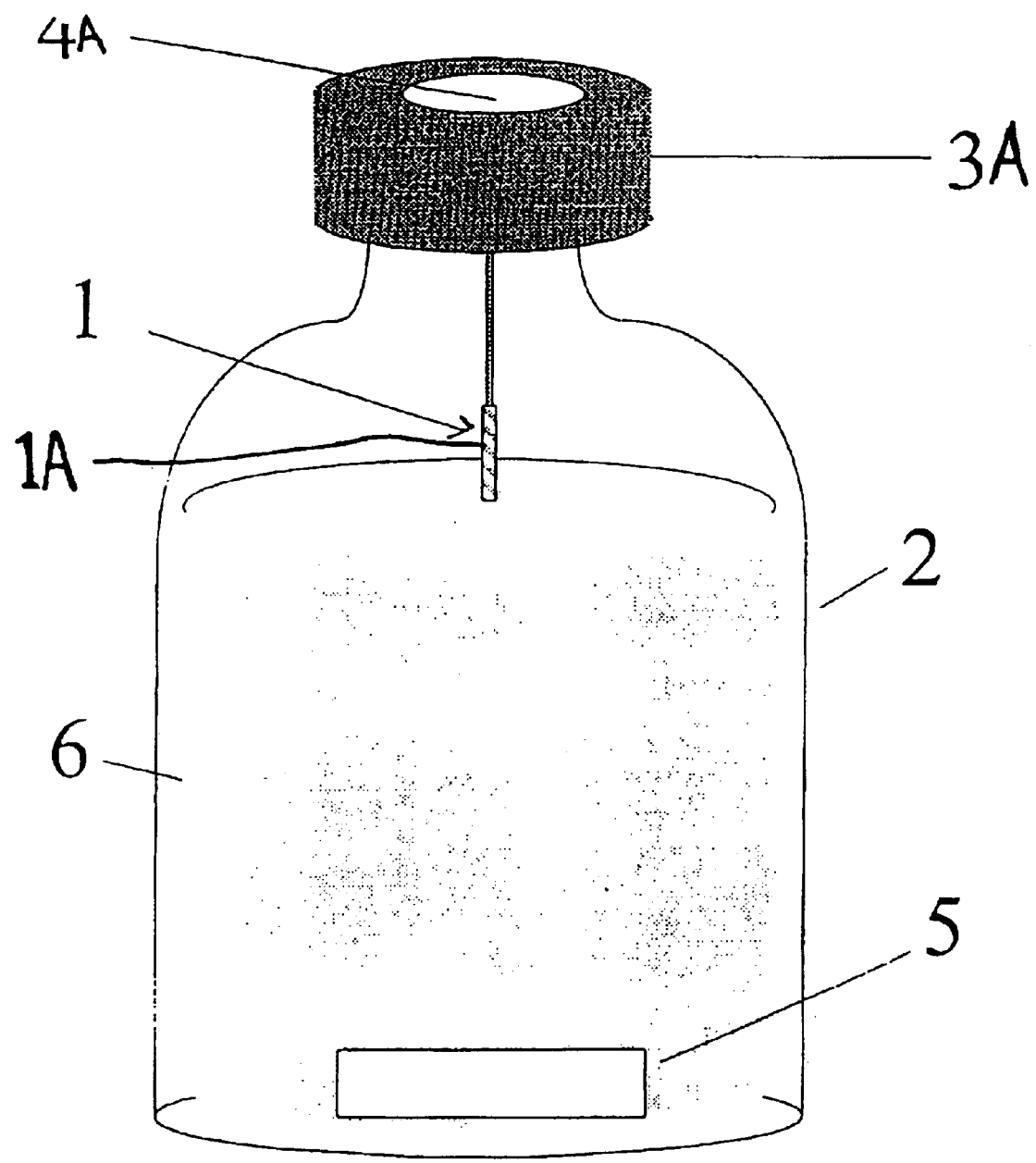
FIG. 4 is a schematic side view of a fibre assembly installed in a typical sampling enclosure according to the invention.

In FIG. 4., the assembly 1 is mounted in a gas tight enclosure 2, typically but not exclusively a hypo-vial (trade mark) with an open top, closed by a crimp top (as illustrated) 3A, or screw cap and Teflon-faced seal 4A. Generally, a Teflon coated magnetic stir bar 5 is included to permit agitation of the sample 6 during extraction of the analytes by the fibre 1A. The assembly 1 is positioned for head space sampling but can also used for direct (aqueous layer) sampling as well. Fibres can be manufactured with various coating lengths but 10 mm is the typical length used. Although longer lengths of coating can result in a greater amount of extracted analyte, for our purpose, a 10 mm length completely submerged in a 150 $\mu$L volume of solvent is sufficient for adequate desorption. For multiple extraction chemistries or to increase the extraction efficiency, we would use mixed chemistry coatings or multiple fibres.

Fibres can be constructed with fused silica or other support material chemically or mechanically modified e.g. by roughening of the fibre surface to improve adhesion of the coating, followed by chemical attachment of the desired coating. Although there are both absorption and adsorption-type SPME coatings available, our fibres with a silicone coating would extract analytes by absorption, while porous polymer coatings (such as Carboxen™) can extract suitable analytes by adsorption within the pore structure.

Alternatively, the support can be constructed from silicone (such as Dow Corning Silastic® Q7-4750 (0.51 mm ID, 0.94 mm OD) that was used in our studies) or other polymer tubing lengths, swelled by solvent and then dried (to a tight fit) over metal wire or other cylindrical support material. Polymer tubing used for the support is exhaustively extracted by solvent to virtually eliminate background levels of extractives prior to use, and then heated to 100° C. for 30 min before use to eliminate any volatiles that may have been absorbed during storage.

The micro extraction technique consists of several simple steps. For example, when a water sample is to be analyzed for certain analytes, it is placed in a hypo-vial (trade-mark) or other suitable gas tight enclosure. The assembly 1 is inserted through the Teflon face of the vial seal into the silicone backing. If a shielded fibre assembly (FIG. 3) is used, the support material extends through the vial seal. Single or multiple fibres can be provided with identical or different coatings. The vial is then made gas tight by crimping the seal into position. Other sealing techniques such as screw cap enclosures can be used. A magnetic stir bar 5 which was enclosed with the sample prior to sealing the vial may be included. The sample may also be heated during extraction. The time required for extraction depends on many factors including the analytes being extracted as well as the thickness and type, if any, of coating on the support. However, extraction times would normally range from several to 60 minutes. The vial is then opened and the analytes contained in the fibre desorbed by immersion in a micro volume of solvent (typically 150 $\mu$L) contained in a small conical shaped vial, such as a gas chromatograph autosampler vial. The fibre can remain in the autosampler vial.

If a shielded fibre is used (FIG. 3), the coating is retracted into the stainless steel tubing by pulling the cylindrical support 1A(FIG. 3) into the tube before opening the vial. The fibre assembly is then extended out from the shield into a micro volume of solvent. The extracted analytes are analyzed by injecting portions of the solvent extract into a chromatograph through injection ports. Various injection ports would include "programmable temperature", "split-splitless", "on-column" and "large solvent volume" types.

Careful construction and the typical one-time use of the fibres allows low variation of extraction efficiencies amongst fibres.

EXAMPLE 1

Salmon (5 g), was spiked with monobutyltin, dibutyltin and tributyltin (final concentration 100 ng/g salmon tissue). The sample was then hydrolyzed with tetramethylammonium hydroxide, derivatized with sodium tetraethylborate, and the resulting ethylated analytes then collected by fibre assembly for 60 minutes at room temperature. Analytes were then desorbed into 150 uL of isoctane. Analysis was by capillary gas chromatography-atomic emission spectrometry monitoring the Sn line 326 nm.

Figure 5A:
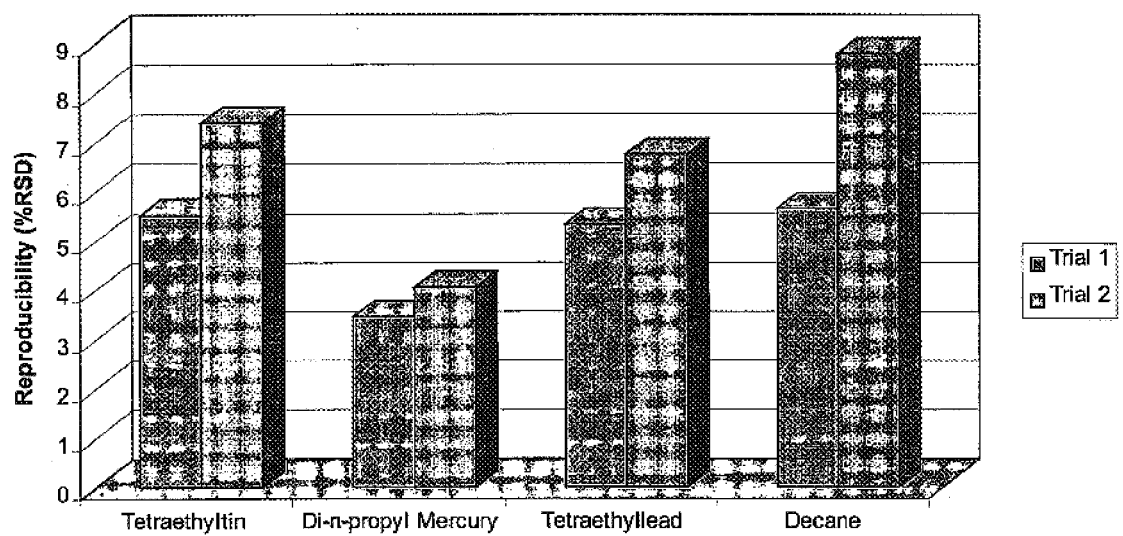
FIG. 5a illustrates the reproducibility of multiple extractions of tetraethyltin, tetraethyllead, di-n-propyl mercury and decane using the present technique from an aqueous solution.
Figure 5B:
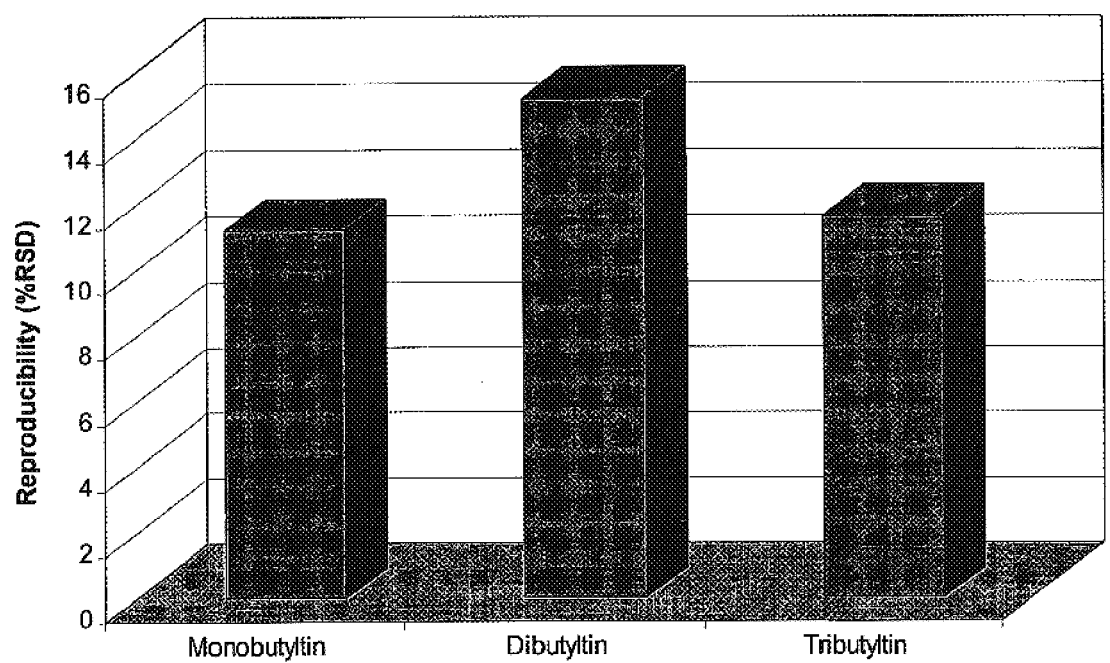
FIG. 5b illustrates the reproducibility of multiple extractions of ionic butyltin compounds (ethylated in situ) from a complex biological matrix using the present technique.

FIG. 5a illustrates that relative standard deviations of extraction for tetraethyllead, tetraethyltin, di-n-propyl mercury and decane (from an aqueous solution spiked at a low ppb level) in two trials of five individual extractions ranged from only 3.5 to 8.8%. FIG. 5b demonstrates that even in the presence of a complex matrix (salmon hydrolysate) low ppb levels of ionic butyltins (derivatized in situ with sodium tetraethylborate) can be reproducibly extracted (11–15% RSD) using the described technique. These results, which are typical for the micro extraction technique, are comparable or superior to other analytical techniques. This consistency enables multiple simultaneous extractions to be conducted without costly automation, greatly enhancing sample throughput and quantitation. Further, since the analytes are desorbed into solvent, the extracts can be easily stored or collected until a convenient time for analysis. Solid phase micro extraction, however, is usually a sequential technique requiring the same device to be used repeatedly—this reduces sample throughput and analysis normally proceeds immediately after sampling. Also, since the analytes are usually thermally desorbed, there is no extract to archive or analyse by alternative analytical instrumentation.

The extraction process of the micro extraction technique is essentially that which occurs with solid phase micro extraction. The simple geometry of the fibre resists clogging from particulates which may be present in the sample matrix. Further, extraction is usually not exhaustive but rather an equilibrium described by the partition coefficient between the water and organic stationary phase for the analytes. Selectivity of the technique can be altered by the appropriate choice of stationary phase for the analytes of interest. The partitioning between the aqueous phase and the organic coating is described by the distribution constant, K:

$$K = C_s/C_{aq} \tag{1}$$

where $C_s$ is the concentration in the stationary phase (coating) and $C_{aq}$ is the concentration of analyte present in the water. Further, assuming a liquid polymeric coating, equation 2 shows that the amount of analyte extracted by the coating at equilibrium can be related directly to its concentration in the sample $$n = (K_{fs} V_f C_o V_s)/(K_{fs} V_f + V_s) \tag{2}$$

where n is the mass of the analyte extracted by the coating, $V_f$ and $V_s$ are the volumes of the coating and sample respectively, $K_{fs}$ is the partition coefficient between the coating and the sample matrix, and $C_o$ is the initial concentration of the analyte in the sample. However, headspace solid phase micro extraction is a three-phase system (equation 3) where n can be expressed as:

$$n = (K_{fh} K_{hs} V_f C_o V_s)/(K_{fh} K_{hs} V_f + K_{hs} V_h + V_s) \tag{3}$$

when $K_{fh}$ is the coating/gas distribution constant, $K_{hs}$ is the gas/sample matrix constant and $V_h$ is the volume of the headspace. A linear relationship therefore exists between the amount of analytes extracted by the coating on the fibre and the initial concentration of these analytes in the sample.

The limit of quantitation depends on the partition coefficient and the thickness of the coating and can extend down to sub part per billion. The rate of the extraction process is essentially the same as for solid phase micro extraction, where initially, the amount of analyte extracted by the coating (stationary phase) increases with increased extraction times until a point of steady state is achieved where the amount of analyte extracted remains relatively constant. At this point a state of equilibrium exists between the concentration of the analyte in the coating, headspace (if present) and in the sample matrix.

EXAMPLE 2

The micro extraction technique is very versatile and can be used for a variety of analytes.

A 50 mL aqueous solution was spiked with a pesticide spike mixture (20–50 ng/uL) containing 1) gamma-BHC (lindane), 2) heptachlor, 3) aldrin, 4) dieldrin, 5) endrin and 6) 4,4'-DDT made up in methanol (final concentration 4–10 ng/mL water). The sample was heated to 70° C. and the analytes collected by fibre assembly for 4 hours. The analytes were then desorbed into 150 uL of issoctane. Analysis was by capillary gas chromatography with electron capture detection.

Figure 6:
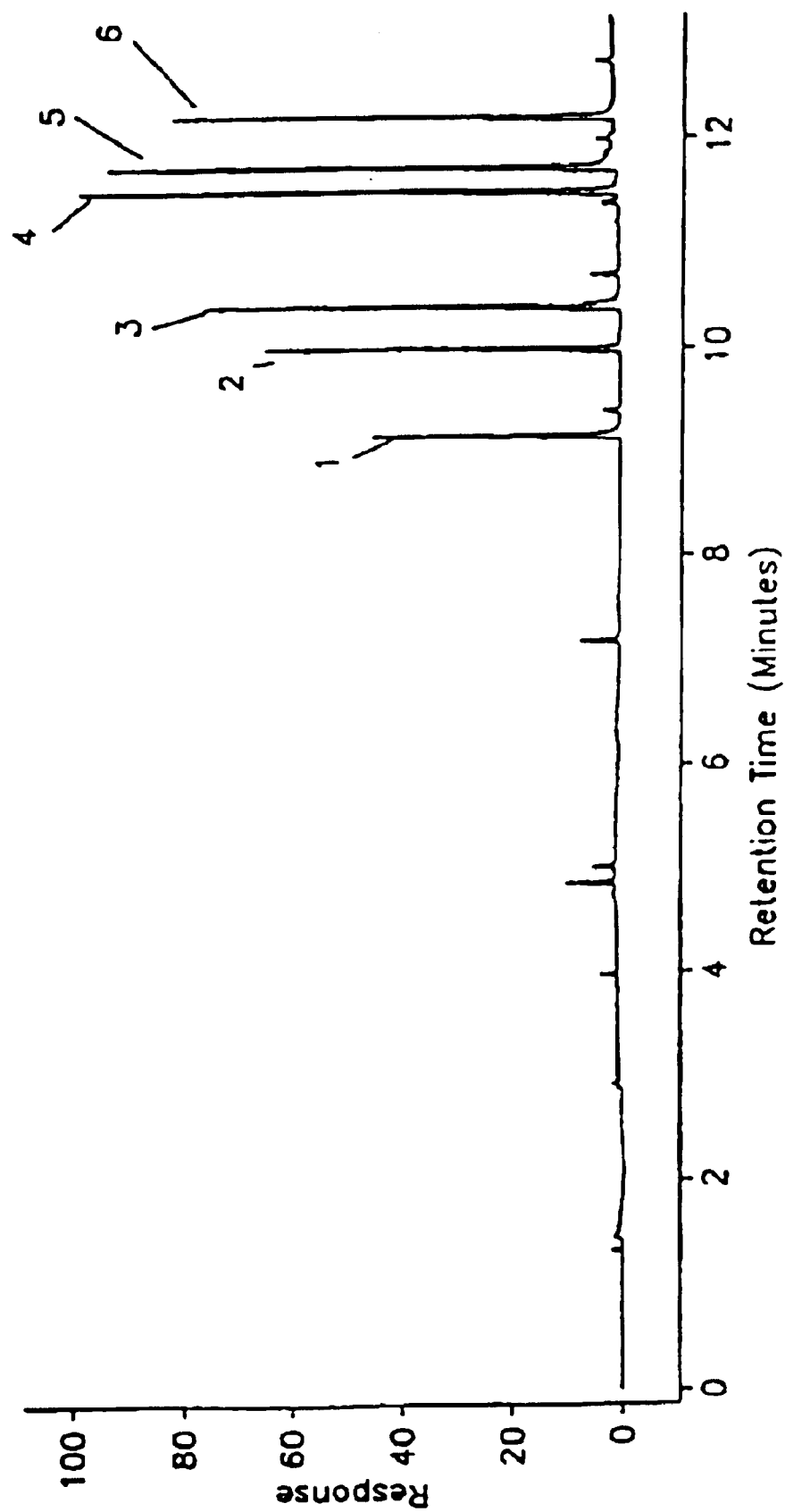
FIG. 6 is a chromatogram of the extraction of a chlorinated pesticide mixture containing 1) gamma-BHC (lindane), 2) heptachlor, 3) aldrin, 4) dieldrin, 5) endrin and 6) 4,4'-DDT from an aqueous sample.

FIG. 6 shows a chromatogram of a chlorinated pesticide mixture (containing of 1) gamma-BHC (lindane), 2) heptachlor, 3) aldrin, 4) dieldrin, 5) endrin and 6) 4,4'-DDT,) extracted from a low ppb-spiked aqueous solution, and analyzed from an aqueous solution by the micro extraction technique with an unshielded silicone coated fibre. The vapour pressure of these compounds range down to 1.5× $10^{-7}$ mm Hg at room temperature, demonstrating that even a relatively nonvolatile compound can be readily quantitated by this technique. A gas chromatograph equipped with an electron capture detector was used for the analysis.

EXAMPLE 3

A 50 mL aqueous solution was spiked with a BTEX mixture (200 ng/uL) containing benzene, ethylbenzene, toluene, m-xylene, o-xylene, and p-xylene made up in methanol (final concentration 40 ng/mL water). The analytes were collected by fibre assembly at room temperature for 60 minutes. The analytes were then desorbed with 150 uL of issoctane. Analysis was by capillary gas chromatography using flame ionization detection.

Figure 7:
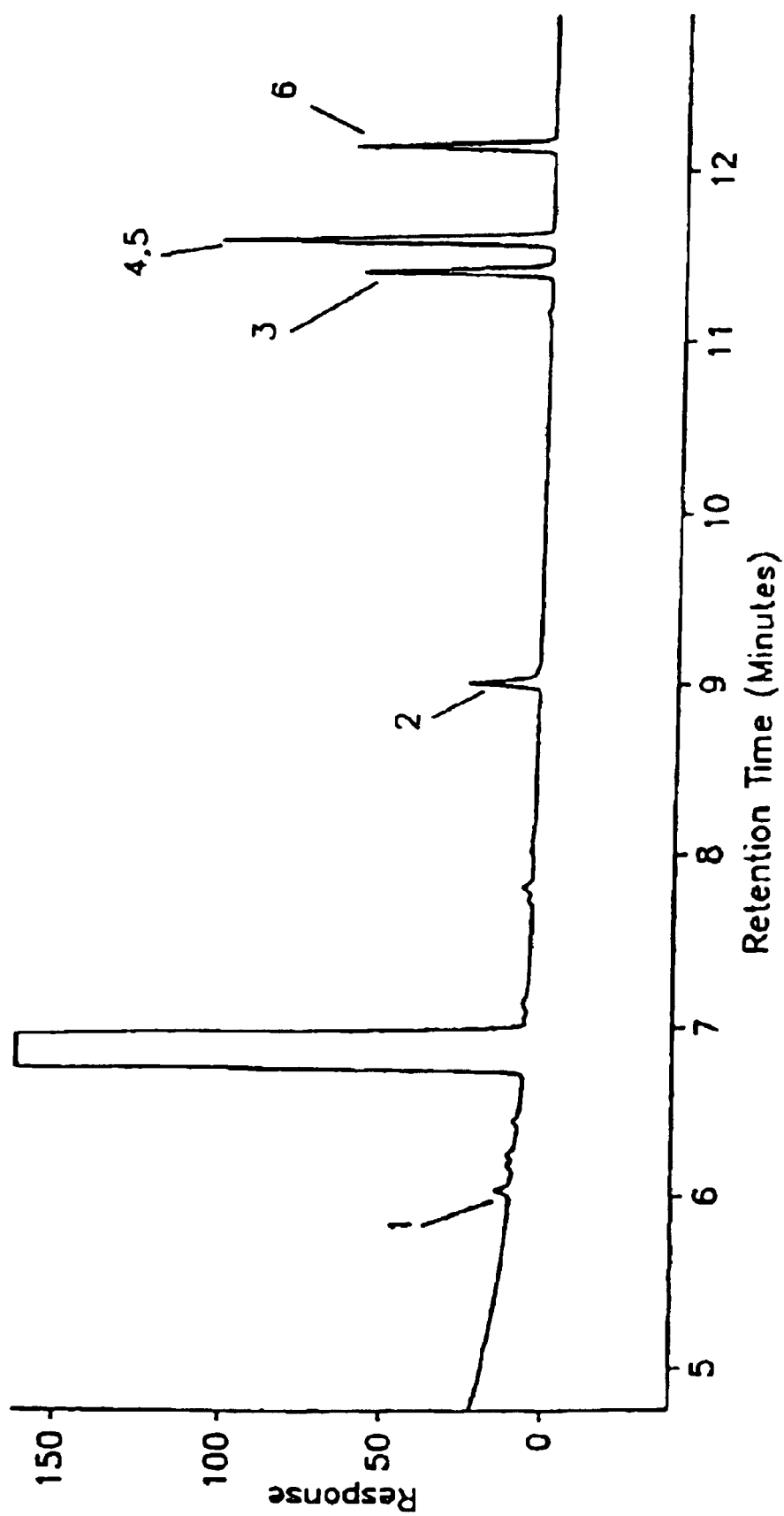
FIG. 7 is a chromatogram of the extraction of a BTEX mixture containing 1) benzene, 2) toluene, 3) ethylbenzene, 4) p-xylene, 5) m-xylene and 6) o-xylene from an aqueous solution.

FIG. 7 shows the chromatogram of a BTEX mixture containing 1) benzene, 2) toluene, 3) ethylbenzene, 4) p-xylene, 5) m-xylene and 6) o-xylene extracted from a low ppb-spiked aqueous solution, and analysed by the micro extraction technique using a unshielded silicone coated fibre. All of the components are present and readily quantitated by FID detector, illustrating that significant sample preconcentration is possible with micro solvent volume desorption of the fibres.

The micro extraction technique can be applied to any analysis suited to solid phase micro extraction since it can be transported for remote sampling, is amenable to existing analytical instrumentation and is quite flexible in terms of coatings. The ability to use multiple fibre assemblies would permit different coating chemistries to simultaneously extract a single sample. Further, since multiple samples can be extracted simultaneously, sample throughput is very high, permitting faster calibration and quantitation of samples.

Fibres of various materials can be used depending upon the intended use, includng fused silica, graphite, various solid polymers and metals.

Examples of fibre coatings include: Carbowax (trade mark for polyethyleneglycols and methoxypolyethyleneglycols), silicone, polyimide, divinylbenzene, polyacrylate, carbon-based sorbents, ion-exchange materials and other materials readily apparent to skilled chemical analysts including those described in U.S. Pat. No. 5,691,206, the disclosure of which is incorporated herein by reference.

The solvent may be any suitable organic solvent known to those skilled in the art of chemical analysis e.g. isoctane.

The micro extraction technique can be used with many different analytical methods, including gas, liquid or supercritical fluid chromatography, atomic absorption or emission, mass spectrometry, and infrared absorption spectrometry.

It will also be appreciated that the method and apparatus according to the invention can be used for analysing not only environmental, biomedical and pharmaceutical samples, but also industrial process streams, chemical reactions, and air monitoring. Further applications will be readily apparent to those skilled in the art.

What is claimed is:

1. An apparatus for carrying out solid phase microextraction of target analytes included in a fluid or a solid sample, comprising gas tight enclosure means for receiving the sample before the enclosure is made gas tight, means located within the enclosure means for extracting the target analytes from the sample, and means located outside of the enclosure means for chemically desorbing the target analytes by solvent extraction by a micro-volume of solvent, wherein the extraction means includes a solid support in the form of multiple fibres which may be coated or uncoated, the fibres and/or the coating being selected, based upon selectivity of the fibres and/or coating for multiple analytes present in the sample, and for simultaneous extraction of the multiple analytes, and wherein the extraction means either samples a head space near the sample or samples the sample directly, and additionally comprising means for shielding the fibers from the atmosphere, such that the fibers are drawn up inside the shield means, providing a tight fit between the fibers and the shield, and the extracted analytes are shielded from volatizing into the atmosphere.

2. An apparatus according to claim 1, wherein the coating is an organic material selected from the group consisting of polyethyleneglycol and methoxy polyethyleneglycol, silicone, polyimide, divinylbenzene, polyacrylate, carbon-based sorbents and ion-exchange materials.

3. An apparatus according to claim 1, wherein the fibers are of a material selected from the group consisting of fused silica, graphite, solid polymers and metals.

4. An apparatus according to claim 1, wherein the fibres are of fused silica, and the coating is of silicone.

5. An apparatus according to claim 1, wherein the fibers are solid fibers or hollow fibers.

6. An apparatus according to claim 5, wherein the coatings are selected from absorption- and adsorption-type coatings.

7. An apparatus according to claim 5, wherein the coatings are identical or different.

8. An apparatus according to claim 5, wherein the fibers are hollow fibers, coated on the outside or the inside.

9. An apparatus according to claim 1, wherein the extraction means is positioned to sample a head space near the sample.

10. An apparatus according to claim 1, wherein the extraction means is positioned to sample the sample directly.

11. An apparatus according to claim 1, wherein the extraction means is positioned to sample both a head space near the sample and to sample the sample directly.

12. A method for solid phase micro extraction of analytes included in a fluid or a solid sample, comprising (a) exposing a fluid or a solid sample including target analytes in a gas-tight enclosure, to a solid support in the form of multiple fibers which may be coated or uncoated, the fibers and/or the coating being selected based upon selectivity of the fibers and/or coating for at least one of the multiple analytes in the sample, and for simultaneous extraction of the multiple analytes for a sufficient time to permit chemical extraction of the analytes by the fibers to occur, wherein the multiple fibers either samples a head space near the sample or samples the sample directly, and (b) ending said exposure, and drawing the fibers up inside a shield means providing a tight fit between the fibers and the shield, such that the extracted analytes are shielded from volatizing into the atmosphere and then placing said solid support into a micro volume of solvent where chemical desorption of the analytes from the support occurs.

13. A method according to claim 12, wherein the solvent is a suitable organic solvent.

14. A method according to claim 12, wherein the chemical extraction is by absorption or adsorption of the target analyte by the fibers or coating.

15. A method according to claim 12, wherein the fibers are uncoated.

16. A method according to claim 15, wherein the fibers are of fused silica.

17. A method according to claim 12, wherein the coating is an organic material selected from the group consisting of polyethyleneglycol, methoxypolyeythyleneglycol, silicone, polyimide, divinylbenzene, polyacrylate, carbon-based sorbents and ion-exchange materials.

18. A method according to claim 17, wherein the coating is silicone.

19. A method according to claim 12, including the additional step of (d) storing and archiving the microvolume of solvent containing the dissolved analytes until a convenient time for analysis.

20. A method according to claim 12, wherein the multiple fibers are positioned to sample a head space near the sample.

21. A method according to claim 12, wherein the multiple fibers are positioned to sample the sample directly.

22. A method according to claim 12, wherein the multiple fibers are positioned to sample both a head space near the sample and to sample the sample directly.

* * * * *